US00PP19426P2

(12) United States Plant Patent
Deroose

(10) Patent No.: US PP19,426 P2
(45) Date of Patent: Nov. 4, 2008

(54) ***POGONATHERUM* PLANT NAMED 'BA50002'**

(50) Latin Name: *Pogonatherum paniceum*
Varietal Denomination: BA50002

(75) Inventor: Paul Deroose, Apopka, FL (US)

(73) Assignee: Deroose Plants Inc., Apopka, FL (US)

( * ) Notice: Subject to any disclaimer, the term of this patent is extended or adjusted under 35 U.S.C. 154(b) by 0 days.

(21) Appl. No.: 11/804,611

(22) Filed: May 19, 2007

(51) Int. Cl.
*A01H 5/00* (2006.01)

(52) U.S. Cl. ..... Plt./384

(58) Field of Classification Search ..... Plt./384
See application file for complete search history.

*Primary Examiner*—Annette H Para

(57) ABSTRACT

A new cultivar of *Pogonatherum* plant named 'BA50002' that is characterized by green leaves and a compact growth habit.

1 Drawing Sheet

Botanical classification: *Pogonatherum paniceum.*
Variety denomination: 'BA50002'.

BACKGROUND OF THE INVENTION

The present invention relates to a new and distinct cultivar of *Pogonatherum* plant botanically known as *Pogonatherum paniceum* and hereinafter referred to by the cultivar name 'BA50002'.

The new cultivar was discovered as a single plant by the inventor in a greenhouse in a cultivated area of Boskoop, The Netherlands in 2002. 'BA50002' was discovered as a naturally occurring whole plant mutation within a population of unnamed *Pogonatherum paniceum* plants. The exact parents are unknown.

Asexual reproduction by tissue culture of the new cultivar 'BA50002' was first performed in 2003 in Evergem, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Pogonatherum* cultivar 'BA50002'.

1. *Pogonatherum* 'BA50002' exhibits green leaves.
2. *Pogonatherum* 'BA50002' exhibits a compact growth habit.

The closest comparison cultivar is *Pogonatherum* 'Monica'. The new cultivar 'BA50002' is distinguishable from 'Monica' by the following characteristics:

1. 'BA50002' has a more compact habit.

BRIEF DESCRIPTION OF THE DRAWING

The accompanying photograph illustrates the distinguishing traits of *Pogonatherum* 'BA50002'. The plant in the photograph shows an overall view of a 16 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Pogonatherum* cultivar named 'BA50002'. Data was collected in Evergem, Belgium from 16 week old greenhouse grown plants in 10 cm containers. The time of year was Winter and the average temperature was 21 degrees Centigrade during the day and 21 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'BA50002' has not been tested under all possible conditions and phenotypic differences may be observed with variations in environmental, climatic, and cultural conditions, however, without any variance in genotype.

Botanical classification: *Pogonatherum paniceum* 'BA50002'.
Use: Ornamental.
Parentage: 'BA50002' is a naturally occurring whole plant mutation of an unknown Pogonatherum cultivar.
Vigor: Moderate.
Growth rate: 5 cm per month.
Growth habit: Broad upright.
Plant shape: Broad inverted triangle to flattened globose.
Suitable container size: 10 cm diameter container.
Height: Average 17.7 cm in height.
Width: Average 29.4 cm in width.
Hardiness: USDA Zone 10.
Propagation: Tissue culture.
Time to initiate roots: Approximately 10–14 days in the summer and 15–20 days in the winter.
Time to produce a rooted cutting or liner: Approximately 35 days in the summer and 56 days in the winter.
Root system: Fine and fibrous.
Lateral branches: Branches growth directly from the roots.
*Pinching.*—Required.
*Number of lateral branches.*—Average 46.
*Lateral branch length.*—11.3 cm.
*Lateral branch diameter.*—0.8 mm.
*Internode length.*—1.3 cm.
*Lateral branch shape.*—Dull and rounded.

*Lateral branch aspect.*—Smooth.
*Lateral branch strength.*—Strong.
*Lateral branch color.*—144B.
*Pubescence.*—Absent.

Foliage:

*Texture.*—Smooth and dull.
*Leaf arrangement.*—Alternate.
*Compound or single.*—Single.
*Leaf shape.*—Narrow lanceolate.
*Leaf apex.*—Acute.
*Leaf base.*—Sheating.
*Leaf length.*—Average 3.5 cm in length excluding sheath, 4.8 cm. including sheath.
*Leaf width.*—8 mm in width.
*Quantity of leaves per lateral branch.*—Average 17 including branchlets.
*Pubescence.*—No leaf pubescence on leaf blade, margins of the sheaths sparsely covered with 0.8 mm. length hairs, 157D.
*Leaf margin.*—Entire.
*Vein pattern.*—Parallel.
*Young leaf color* (*upper surface*).—144C with veins 144A.
*Young leaf color* (*lower surface*).—144C with veins 144A.
*Mature leaf color* (*upper surface*).—137A.
*Mature leaf color* (*lower surface*).—137B.
*Vein color* (*lower surface*).—137B.
*Vein color* (*upper surface*).—137A.
*Leaf attachment.*—Petiolate.
*Durability of foliage to stress.*—Moderate.

Flowers: *Pogonatherum* 'BA50002' does not produce flowers.

Disease and Insect Resistance: Plants of the new *Pogonatherum* have not been observed for disease or insect resistance.

What is claimed is:

1. A new and distinct variety of *Pogonatherum* plant named 'BA50002' as described and illustrated.

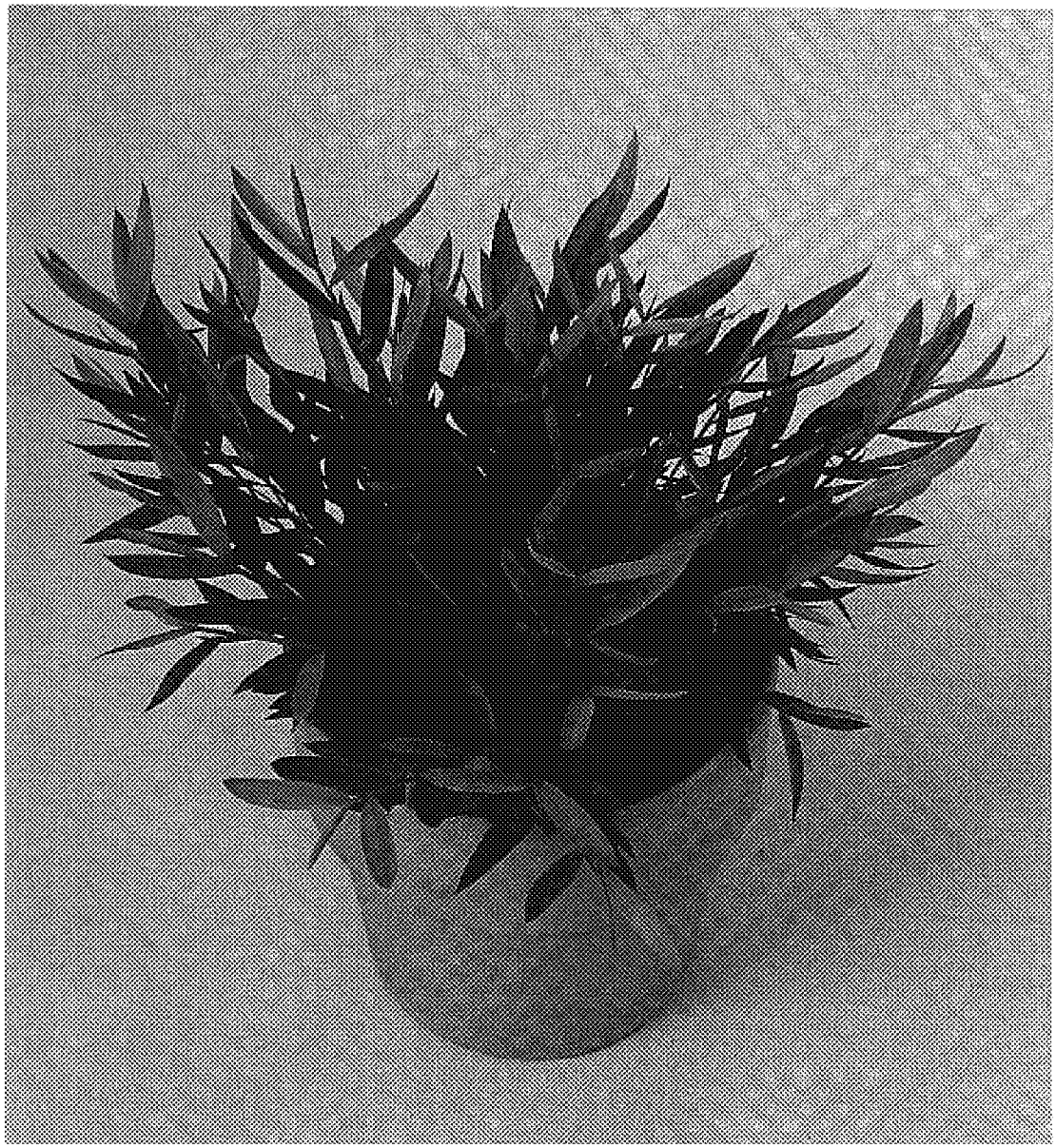

* * * * *